US012762626B2

(12) United States Patent
Navani et al.

(10) Patent No.: US 12,762,626 B2
(45) Date of Patent: Oct. 13, 2026

(54) ELECTRONIC COMMUNICATION PLATFORM AND APPLICATION

(71) Applicant: Le Reve Regenerative Wellness Inc., Campbell, CA (US)

(72) Inventors: Annu Navani, Campbell, CA (US); Raj Navani, Campbell, CA (US)

(73) Assignee: Le Reve Regenerative Wellness Inc., Campbell, CA (US)

( * ) Notice: Subject to any disclaimer, the term of this patent is extended or adjusted under 35 U.S.C. 154(b) by 134 days.

(21) Appl. No.: 17/675,496

(22) Filed: Feb. 18, 2022

(65) Prior Publication Data

US 2022/0262518 A1 Aug. 18, 2022

Related U.S. Application Data

(60) Provisional application No. 63/150,991, filed on Feb. 18, 2021.

(51) Int. Cl.

*G06Q 40/08* (2012.01)
*G16H 10/60* (2018.01)
*G16H 50/20* (2018.01)

(52) U.S. Cl.

CPC .......... *G06Q 40/084* (2025.08); *G06Q 40/08* (2013.01); *G16H 10/60* (2018.01); *G16H 50/20* (2018.01)

(58) Field of Classification Search

CPC ........ G06Q 40/08; G16H 10/60; G16H 50/20; G16H 15/00; G16H 20/40; G16H 40/20; G16H 40/67; G16H 50/70; G16H 80/00

See application file for complete search history.

(56) References Cited

U.S. PATENT DOCUMENTS

| | | | | |
|---|---|---|---|---|
| 7,337,121 | B1 | 2/2008 | Beinat | |
| 11,537,888 | B2 * | 12/2022 | Banisakher | G06N 3/0985 |
| 2007/0027714 | A1 | 2/2007 | Fenno | |
| 2008/0214903 | A1 * | 9/2008 | Orbach | A61B 5/165 705/2 |
| 2011/0099116 | A1 | 4/2011 | Gabel | |
| 2016/0005320 | A1 * | 1/2016 | deCharms | G09B 19/00 434/236 |
| 2016/0350509 | A1 * | 12/2016 | Sharma | A61B 5/02055 |

(Continued)

FOREIGN PATENT DOCUMENTS

WO WO-2014124002 A1 * 8/2014 ............ A63F 13/00

OTHER PUBLICATIONS

Qin, Jin, et al., "The Impact of Workplace Factors on Filing of Workers' Compensation Claims Among Nursing Home Workers", BMC Musculoskeletal Disorders, vol. 15, No. 29, Springer, 2014 (Year: 2014), 9 pages.

*Primary Examiner* — Rachelle L Reichert
(74) *Attorney, Agent, or Firm* — Sheppard Mullin Richter & Hampton LLP

(57) ABSTRACT

Systems and methods are provided for a medical software platform for providing therapies to a patient user. For example, the medical software platform can receive patient data and determine a patient state. The medical software platform can interact with the user device to provide one or more therapies associated with artificial intelligence (AI), robotics, and/or extended reality (XR). With this combination, the medical software platform can effectively diagnose and alleviate pain in various environments, including in a metaverse or other online scenario.

19 Claims, 8 Drawing Sheets

(56) References Cited

U.S. PATENT DOCUMENTS

| | | | |
|---|---|---|---|
| 2017/0255754 A1 | 9/2017 | Allen | |
| 2018/0193650 A1* | 7/2018 | Srivastava | A61B 5/02416 |
| 2020/0342969 A1 | 10/2020 | White | |
| 2022/0237878 A1* | 7/2022 | Tartz | G06F 3/14 |
| 2022/0262518 A1 | 8/2022 | Navani | |

* cited by examiner

ELECTRONIC COMMUNICATION PLATFORM AND APPLICATION

CROSS REFERENCE TO RELATED APPLICATIONS

This non-provisional patent application claims priority from U.S. Patent Application No. 63/150,991, filed Feb. 18, 2021, the contents of which are incorporated by reference in their entirety.

DESCRIPTION OF RELATED ART

Medical data is often time sensitive, yet the systems configured to provide medical data often delay transmission of the data. Better systems are needed.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

The figures are not exhaustive and do not limit the present disclosure to the precise form disclosed.

DETAILED DESCRIPTION

Pain can result from any structure of human body including bones, soft tissues or other nerves, muscles, ligaments, cartilage, tendons, or discs. It can be acute or chronic, and may be a life-long issue for the patient. Some pain can be associated with actual structural tissue damage such as a bone fracture or spine disc injury, while other pain may result without tissue damage such as Complex Regional Pain syndrome. When the pain does not result from tissue damage, there may be no inciting event. The nerves may enter a state of hyperexcitability and fire, which can increase pain signals to the brain and lead to loss of use of the limb, or even pain in an absent body part (e.g., post amputation pain in the place of previous limb).

The details and specifics relating to the cause of some pain remains unsolved. For example, the biopsychosocial model of pain focusses on addressing biological, physical, and psychological aspects of pain, but pain can still exist.

Embodiments of the application provide pain management in a technological environment using a patient user device and medical software platform. The patient user device may incorporate various rehabilitation therapies (e.g., mental, psychological, or behavioral rehabilitation), nutritional counseling, yoga, mindfulness, or vocational counseling to provide therapy suggestions to the patient. The medical software platform interacts with the user-based application using artificial intelligence (AI), robotics, and/or extended reality (XR). For example, the medical software platform can receive a medical profile or other information from the patient or physician to store with the patient profile. Portions of the patient profile may be provided to a machine learning model to help determine when the patient is ready to receive different or additional therapies to prescribe to the patient to increase health. With this combination, the medical software platform can effectively diagnose and alleviate pain through technological means in various environments, including in a metaverse or other online scenario, to improve the technical/human interaction environment. As such, the user-based application can Technical advantages are realized throughout. For example, traditional processes may rely on guessing which therapies to provide to a patient without use of the technologies available through the medical software platform and corresponding user-based application. By incorporating artificial intelligence, robotics, and/or XR, the devices may be able to quickly identify portions of a user profile that would benefit from these technological therapies and transmit electronic communication that can be interacted with at the user-based application to improve the patient's health.

Figure 1:
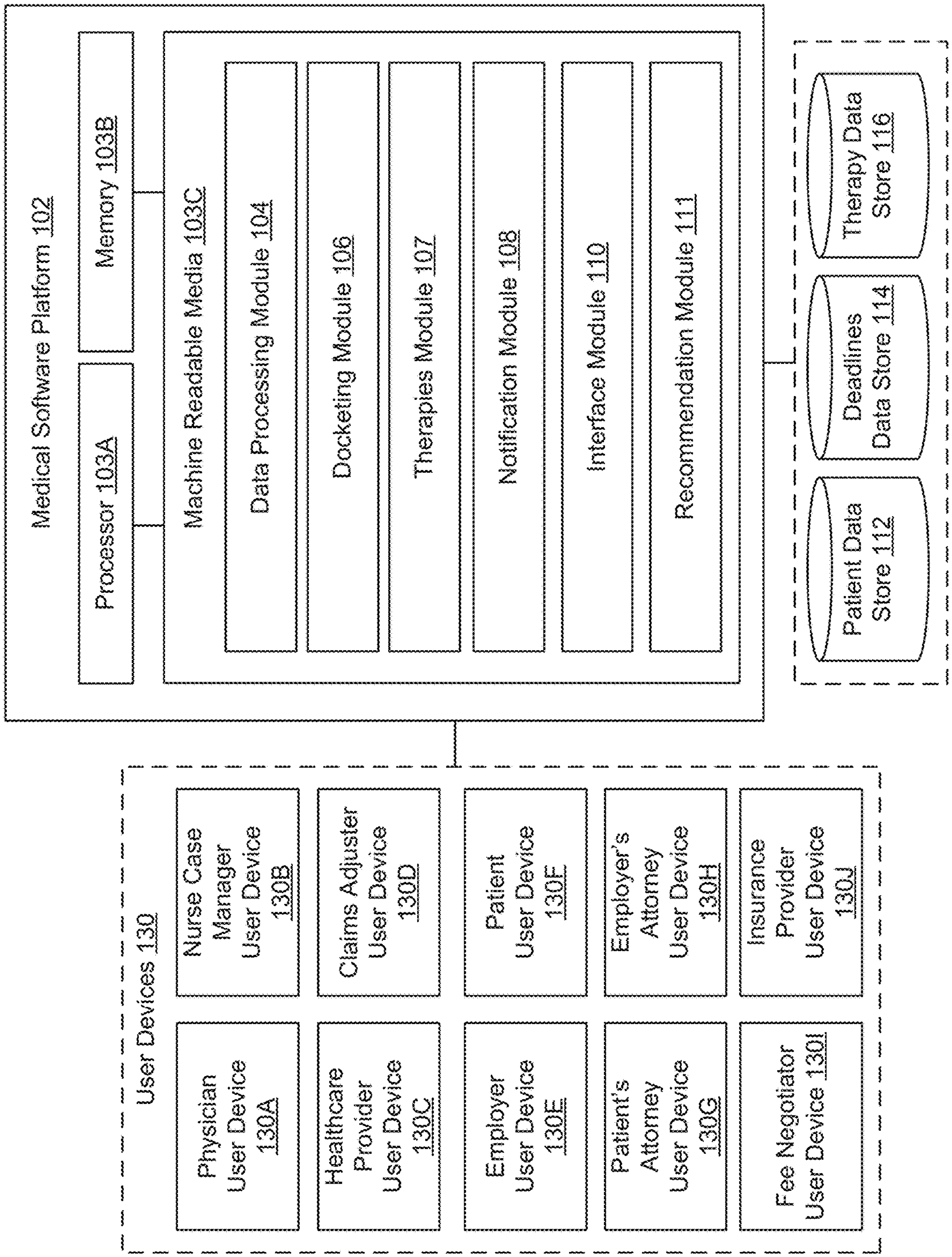
FIG. 1 illustrates a medical software platform and one or more user devices, in accordance with embodiments of the application.

FIG. 1 illustrates a medical software platform and one or more user devices, in accordance with embodiments of the application. Medical software platform 102 and one or more user devices 130 may communicate via a network.

Medical software platform 102 may comprise one or more processors, controllers, control engines, or other processing devices, such as processor 103A. Processor 103A might be implemented using a general-purpose or special-purpose processing engine such as, for example, a microprocessor, controller, or other control logic.

Medical software platform 102 might also include one or more memory 103B and machine readable media 103C. For example, memory 103B and/or machine readable media 103C may comprise random-access memory (RAM) or other dynamic memory, might be used for storing information and instructions to be executed by processor 103A. Memory 103B and/or machine readable media 103C might also be used for storing temporary variables or other intermediate information during execution of instructions to be executed by processor 103A. Memory 103B and/or machine readable media 103C might likewise include a read only memory ("ROM") or other static storage device coupled to a bus for storing static information and instructions for processor 103A.

Medical software platform 102 may comprise one or more modules that perform processes or operations. The modules may include, for example, data processing module 104, docketing module 106, therapies module 107, notification module 108, interface module 110, and recommendation module 111.

Data processing module 104 may receive and process data from various data sources. For example, data processing module 104 may provide an application programming interface (API) to receive and provide data in a predetermined format (e.g., structured data). Other types of data may be received and parsed according to a text processing algorithm or optical character recognition (OCR). The data may be stored in patient data store 112.

Data processing module 104 (with interface module 110) may generate a visual workflow of the data. For example, the visual representation of the path that the data take through the process, analysis, and current state of the patient by presenting data along an illustrative path using visual process elements.

The patient state may help identify a pain level of the patient from patient data. In some examples, the patient state may correspond with the patient experiencing one or more pain symptoms. For example, the nerves of the patient may enter a state of hyperexcitability and fire, which can increase pain signals to the brain and lead to loss of use of the limb, or even pain in an absent body part (e.g., post amputation pain in the place of previous limb).

Data processing module 104 may determine a medical record and/or analytics for a patient to determine the patient data. The patient data may include which tests, medical treatments, and therapies have been performed on the patient and how the patient is responding to the therapies (e.g., through test results determined by a lab technician, or through feedback and responses from the patient or physician documenting responses).

As a sample illustration, a therapy for a particular patient may be to perform physical rehabilitation. Data processing module 104 may compare the type of physical rehabilitation and patient data collected from the patient before and after the physical rehabilitation is started with other patients that had similar therapies to help determine how the patient is reacting to the particular therapy. The progression of the patient's health and/or test results (identified in second patient data) may be determined from one or more tests and uploaded in association with a timeline. The health progression of a first patient may be compared to other patients to determine whether the time that the first patient takes to heal and recover is common or different than the other patients. The comparison between the first patient and other patients may help identify commonalities between the timelines, tests, and results in order to determine different therapies and expediting recovery.

In some examples, future therapies may be altered based on the comparison between the first patient and other patients. In this example, the first patient may be originally scheduled to perform twelve physical therapy sessions after a particular type of surgery. The therapy may be adjusted or removed based on the analytics and comparison with the other patients to help increase the likelihood of recovery for the first patient.

Data processing module 104 may compare patient data corresponding to the patient's recovery with approvals or denials of therapies. For example, when an entity denies a therapy for a patient, a timeline of recovery for a plurality of similar patients to the first patient without the therapy may be compared to other patients that received the therapy. Data processing module 104 can predict the length of recovery time for the first patient based on the comparison with other patients with similar attributes, and provide the prediction to one or more user devices 130, including the patient user device 130F, physician user device 130, or healthcare provider user device 130C.

Data processing module 104 may associate a therapy with a status of a patient. The status may include a binary determination (e.g., patient is better or not better, etc.) or a range of values (e.g., 01-10, etc.). The status and corresponding therapy may be stored in patient data store 112.

Data processing module 104 may comprise access control where access to the data is provided upon authentication of the user. The access control may define responsibilities and visibility according to the user's role, access level, and form data. The access controls may limit the accessibility to data and reports in accordance with the determined access level.

Docketing module 106 may determine deadlines and dates associated with data. Docketing module 106 may identify a triggering event (e.g., receiving a request for a new therapy, etc.) and determine a deadline associated with the triggering event (e.g., five days to approve/deny the request, etc.). A notification may be transmitted from medical software platform 102 to one or more user devices 130 to identify the triggering event, response, and deadline. The triggering event and corresponding deadline may be reliant on predetermined rules and stored in deadlines data store 114.

In some examples, docketing module 106 may update deadlines based on feedback from one or more entities. For example, a patient's attorney operating patient's attorney user device 130G may request ten days to produce information while the employer's attorney operating employer's attorney user device 130H may respond with fifteen days. The correspondence between the two entities may be tracked and stored, and/or provided to court authorities as evidence or case management. In some examples, when a deadline is updated, various systems may be automatically triggered to update as well. Medical software platform 102 may generate and transmit notifications of the updates, or automatically update data in the patient data store 112 or similar data repository. This may include docketing module 106 to update deadlines data store 114 with the new deadline and notification module 108 to alert one or more entities of the new deadline.

In another example, a physician may request that the patient lifts ten pounds to return to work, but the employer requests that the patient lift fifteen pounds to return to work. The correspondence between the two entities may be tracked and stored, and other processes may be triggered as well. For example, additional therapies may be ordered and requested for approval (e.g., from a claims adjuster, etc.) in order to ensure that the patient reaches the fifteen pound requirement.

In some examples, the therapy may be associated with an occupation of the patient or other information. For example, the fifteen pound requirement may be associated with a carpenter but not a data analyst, so the therapies to help the patient work up to lifting fifteen pounds may be required for the carpenter but not the data analyst.

Therapies module 107 may determine one or more therapies associated with a health of a patient user, including AI, robotics, and augmented reality (AR), virtual reality (VR), mixed reality (MR), or other extended reality (XR) technology. Any of these therapies may be used to diagnose and treat pain, individually or in any combination with each other. Any condition may be treated with these therapies, including health issues associated with pain, or pain related physical or mental disorders.

For artificial intelligence (AI), medical software platform 102 may track a patient's presentation of symptoms in accordance with a timestamp (using data processing module 104). The symptoms and timestamps may be stored in patient data store 112. Therapies module 107 may receive second or subsequent patient data and compare the patient's symptoms from the first and second patient data over time to determine the pattern of symptoms. The pattern of symptoms may be compared with a plurality of pain profiles and/or a current state of a patient. When the correlation of pain symptoms over time correspond with a pain profile, the patient may be determined to match the pain profile. In some examples, each of the one or more pain profile may match with one or more therapy regimes stored in therapy data store 116. When the patient matches the pain profile, the corresponding therapy regime may be determined by therapies module 107 and provided to the patient user device 130F for a specific and individualized therapy plan for the patient.

Therapy plans and their associated effectiveness may be tracked. For example, the date that the therapy was transmitted may be stored in the patient data store 112 along with patient feedback associated with the therapy. The feedback data may be compared to other patient data, including demographics or a list of medical issues or socio-economic conditions to determine any correlations when a plurality of patients have similar feedback to similar therapies along a similar timeline. The therapy plan for the first patient may be updated to a therapy plan implemented for other patients when those therapy plans previously were effective. New therapy plans may be evaluated and compared against prior therapy plans with respect to the patient data to predict future effectiveness for the patient.

Using robotics, therapies module 107 may implement a pain distraction process to provide pain management. For example, the distraction process may begin with a physical examination to identify and diagnose the pain location and intensity. The physical examination may be implemented using imaging (e.g., from a camera incorporated with the patient user device 130F or physician user device 130A) or electrodiagnostic review to generate patient data. The patient data may be reviewed and interpreted to corroborate the diagnosis of the pain location and pain intensity. Once the pain location and intensity is determined, a robot can help further analyze the body movements (e.g., determining a range of motion, providing a stimulation and measuring a response, etc.).

In some examples, a robot may be implemented to provide the pain management. For example, using the diagnosis of the pain location and intensity, a robot may apply acupressure, acupuncture, pain injections, trigger point identification and release, physical therapy, or stretching, among other therapies.

In some examples, a robot may help generate patient data. For example, the robot may incorporate embedded or external sensors. The sensors may measure strength, sensation, range of motion, posture, gait, skin conduction, muscle activity, oxygen level, hydration, Body Mass Index (BMI), biometric impedance analysis, brain activity, glucose, sleep, mood, activity, heart rate, respiration, pulse, blood pressure, and other bodily functions.

In some examples, therapies module 107 may combine technologies, including AI and robotics, to provide a therapy for the patient. For example, AI can determine a similar pain identifier and AI can determine other similar patients with similar pain identifiers, in addition to identifying therapies that may have reduced the other patients pains.

In some examples, AI can identify pain generators and generate therapy profiles based on the diagnosis. The therapy profiles may include, for example, muscle repair or nerve release.

In some examples, AI can predict sore spots, pain points, or trigger points on the patient's body. The prediction of these locations of pain can be determined using either an analysis of patient's reported symptoms or robots with sensors. When robots are used, the sensors associated with the robots can measure an amount of pressure to apply at each point of the patient's body to get relief from the corresponding pain.

In some examples, AI can store individualize parameters and compare to standard. Prior and current data points help in determining the optimum care.

In some examples, AI can recommend changes for change in the therapy when the patient state (e.g., the level of pain that the patient is experiencing) exceeds a threshold value. The one or more therapies may be identified by the AI based on similar patients or symptoms, based on new therapies that are available at a geographical location, or other factors. The one or more therapies may be identified that correspond with a decreased level of pain and other patients.

In some examples, AI can combine therapy programs to generate a new therapy program or patient profile. The combination of therapies may be identified by symptoms, prior experience with similar profile patients, and/or the associated therapies.

Using AR, VR, MR, or XR technology (used interchangeably for illustrative purposes), therapies module 107 can analyze pain of the patient from the user-based application. For example, XR technology can assist with pain interventions or surgeries using 4D imaging as well as tissue-guided imaging techniques. The pain interventions or surgeries can be performed in association with XR devices to map a patient's body, the surgical procedure being performed, or visualizing any aspects of the therapy process.

In some examples, XR technology can provide physical rehabilitation of spine, joints, muscles, nerves, or other physical locations. For example, XR can help with neuroplasticity and decrease transmission of pain signals to the brain by displaying a virtual environment to distract the patients during the therapy. The virtual environment may correspond with digital scenarios developed for XR devices.

In some examples, XR technology can provide mental rehabilitation. For example, XR may provide therapies to remediate depression, anxiety, attention-deficit/hyperactivity disorder (ADHD), social anxiety, or mental disorders when these disorders are paired with pain. This is achieved by scenarios developed for XR devices that may distract the patients during the therapy and they come back for more scenarios. This helps them better cope with mental health conditions.

In some examples, XR technology can provide individual or group cognitive behavioral therapy sessions. For example, therapies module 107 may determine a first avatar or other digital image of the patient in a meeting space with a second avatar or other digital image of the physician. Additional avatars or digital images of patients may be present in the digital space as well. The physician may lead the therapy session of the digital images to provide the treatment for the patient's health issue.

Similarly, XR technology can be used to provide nutritional coaching, vocational training, wellness classes, yoga classes, leading a mediation session, fitness classes, or other digital environments where the therapy provided by therapies module 107 is implemented.

In some examples, XR technology can provide games for maintenance therapy of pain interventions, surgeries, physical rehabilitation, mental rehabilitation, cognitive behavioral therapy session, nutritional coaching, vocational training, wellness classes, yoga classes, leading a mediation session, fitness classes, or other scenarios where games may be implemented.

These and other therapies implemented by therapies module 107 may be provided to the patient operating patient user device 130F or other user device 130. For example, when AI is implemented, patient user device 130F may present a survey to gather feedback from the patient. The feedback may be transmitted to therapies module 107 via a network and provided to a trained model that can identify similar patients with similar feedback. The therapies that reduced the pain symptoms for those patients may be suggested for the current patient, despite or in addition to consideration of the physical location, demographic, or socio-economic differences. When robotics are implemented, patient user device 130F may be implemented as the robot device or sensors that perform the therapy or gather the patient data. The robot/patient user device 130F can receive the suggested movements from therapies module 107 and transmit the patient data back to medical software platform 102. When XR is implemented, patient user device 130F may be implemented as the XR device that can present the digital environment, perform the treatment, or gather the patient data. The XR/patient user device 130F can receive the digital environments or other virtual reality from therapies module 107 and transmit the patient data back to medical software platform 102.

Notification module 108 may generate one or more notifications for the plurality of users. The notifications may be predetermined to identify one or more entities that may be alerted to receiving data (e.g., when any data are uploaded to the platform, etc.) or may be determined in real-time (e.g., when the data are uploaded and defined by the uploading user, etc.).

Notification module 108 (in association with docketing module 106) may generate and transmit a notification to a user to identify an upcoming deadline. The notification may identify the data that is requested and request that the user provide the data (e.g., patient data, case report, new therapy suggestion, approval/denial of requested medical treatment or therapy, etc.).

As an illustrative example, notification module 108 may generate and transmit a notification to a patient operating a patient user device 130F or other entity to perform a therapy session or a physician operating a physician user device 130A, in association with performing or suggesting a therapy. The notification to the physician may identify a deadline for providing, reviewing, or analyzing information for responding to the therapy administered to the patient and the notification to the patient may remind the patient to perform the therapy, log back into the system to receive new type of therapy or new therapy session, or other notifications to provide pain management.

Multiple notifications may be generated and transmitted in accordance with the deadline (e.g., to help reduce the patient's pain along a timeline). For example, when the deadline is within a threshold (e.g., within a day or week, etc.), notification module 108 may automatically transmit a second notification to an entity (e.g., to provide the information within the deadline).

Interface module 110 may provide a user interface for receiving and providing patient and case data. The interface may be accessible via a web browser operated at a user device 130.

Interface module 110 may provide a fluid layout. The fluid layout may be generated using one or more user interface tools to create a customizable visual layout of data in an easy to read format with one or more data elements shown together.

Interface module 110 may comprise a customized interface to match the entity and/or user device accessing medical software platform 102. For example, medical software platform 102 may determine the entity accessing medical software platform 102 and adjust the interface (via interface module 110) to provide information in accordance with settings defined by the entity. For example, when the entity prefers to view a monthly therapy report about a patient (e.g., claims adjuster, etc.), the interface may match an identifier or login credential associated with the user device (e.g., as the claims adjuster) to the entity logging in and provide the requested report automatically. Interface module 110 may provide custom and/or standardized forms that allow the entity to adjust everything from reporting and data elements to the data sources.

Recommendation module 111 may generate reports and analytics. For example, recommendation module 111 may determine insights into patient records with customizable dashboards and reports that can give users the information they need to improve the health of the patient within various time constraints.

Recommendation module 111 may access one or more therapies from therapy data store 116 and provide the therapy as a suggestion to the patient. The therapy or other suggestions may be based on the data in the patient user profile and/or added by the physician via the physician user device 130A. The recommendations may be provided virtually to the patient and accessible via the patient user device 130F.

Recommendation module 111 may determine one or more therapies based on the change in feedback over time. For example, at day one, the patient may experience a first level of pain and at day ten, the patient may experience a second level of pain. Based on the change in pain level from the first level to the second level, recommendation module 111 may select a therapy from therapy data store 116 that corresponds with the changing pain level.

Recommendation module 111 may receive patient data directly from the patient. For example, a software application may be installed on patient user device 130F to pose questions to the patient, and the patient can respond to the questions and/or the patient may access the platform via data processing module 104. The data may be stored in patient data store 112 and accessible on a limited basis (e.g., via authentication and verification of entities that are permitted to view the data). The questions may help identify the patient's current mood (e.g., happy, depressed, etc.), pain level (e.g., 0-10, etc.), exercise level (e.g., active, sedentary, etc.), or physical characteristics (e.g., weight, heart rate, blood sugar level, etc.).

In some examples, the change in pain level (or other data metrics) may be compared with a threshold for the particular patient (stored with the patient profile) or for the particular injury. This may include a threshold associated with a first patient that is different than a threshold associated with a second patient. The rate of change compared with the threshold can help determine which therapy should be recommended by the platform (e.g., based on a set of rules of the platform).

In some examples, recommendation module 111 may enable monitoring of patient progress via medical software platform 102, as physicians and other entities engage in various aspects of individual or group therapy. For example, recommendation module 111 may standardize pain scores or other data, including sensor based recordings or self-reported symptoms. In some examples, recommendation module 111 may compare the pain scores or other data to a threshold value. When the pain score exceeds the threshold value, recommendation module 111 can alert health care providers or other entities that the health of the patient is falling below the threshold level. As illustrative examples, the recommendation module 111 may notify the health care provider that the mental health of the patient is at a dangerous level (e.g., below the threshold value), or that the activity or nutritional level is beyond a certain range from a threshold or baseline value.

Recommendation module 111 may provide a functional restoration and chronic pain program that includes individualized therapies for the patient. The therapies may include yoga, physical therapy, psychology, nutrition, pain management, medications, live or pre-recorded lectures, counseling, meditation, and the like.

As sample illustrations, the pain level may increase over time and the therapy suggested to the user may include physical stretching. Recommendation module 111 may identify the stretches that would be helpful for the user based on the profile (e.g., the location of the injury, etc.) or the patient's responses to questions. When the pain level increases and the mood level decreases, the recommendation may include meditation and medication, based on the set of rules and data for recommending these therapies.

Recommendation module 111 may determine one or more therapies based on the change in feedback over time. For example, at day one, the patient may experience a first level of pain and at day ten, the patient may experience a second level of pain. Based on the change in pain level from the first level to the second level, recommendation module 111 may select a therapy from therapy data store 116 that corresponds with the changing pain level.

One or more data stores may comprise patient data store 112, deadlines data store 114, and therapy data store 116. The data stores may comprise a repository of qualified providers that can help provide the therapy session in addition to independent evaluation of third party cases.

Patient data store 112 may comprise complete healthcare data of the patient, including biographical data, test and test results, patient feedback, or other information associated with the health and state of the patient.

Deadlines data store 114 may comprise a list of time limits that may be triggered from receiving or providing data to one or more user devices 130. Each of the time limits may correspond with a triggering event that is associated with a date (e.g., a task must be completed by a certain date) or another action (e.g., a task must be completed in response to the completion of another task).

Therapy data store 116 may comprise a list of therapies that may be suggested to the patient. The therapies may be suggested to the patient upon satisfying one or more conditions of the patient (e.g., patient has X injury that is cured by Y medication, etc.) or when an output of a machine learning model suggests the therapy (e.g., patients with X symptoms in the past have been cured with Y therapies 90% of the time, etc.).

Therapy data store 116 may comprise wellness data. Wellness data may comprise information generated by the patient associated with wellness activities and a corresponding date or duration. Some examples of wellness data correspond with social activities, nutrition, and physical activity.

Once the data are received, medical software platform 102 may aggregate and normalize the data. For example, medical software platform 102 may index, tag, and mine the data for easy organization and faster retrieval. In some examples, the data may be normalized in order to correspond with a pre-existing format in the patient data store 112 (e.g., unstructured to structured data).

Other sources of information may also be added to one or more databases, including patient data store 112, deadlines data store 114, and therapy data store 116. These may include provider inputs, provider recommendations, and/or corresponding appointments. In combining multiple sources of data, medical software platform 102 can act as a data repository for multiple, distributed entities to reduce the patient's pain symptoms. Medical software platform 102 may be a single platform where each entity can request and receive data relating to medical and claims management data for the patient.

Additionally, medical software platform 102 can provide functionality to enable real-time communications between entities associated with pain management. For example, the communications may help share real time data through a portal associated with medical software platform 102 (e.g., via an API accessible with authentication credentials). In some examples, medical software platform 102 may provide the capability for instant messaging and video communication between any combination of the entities, as illustrated with FIG. 2.

Figure 2:
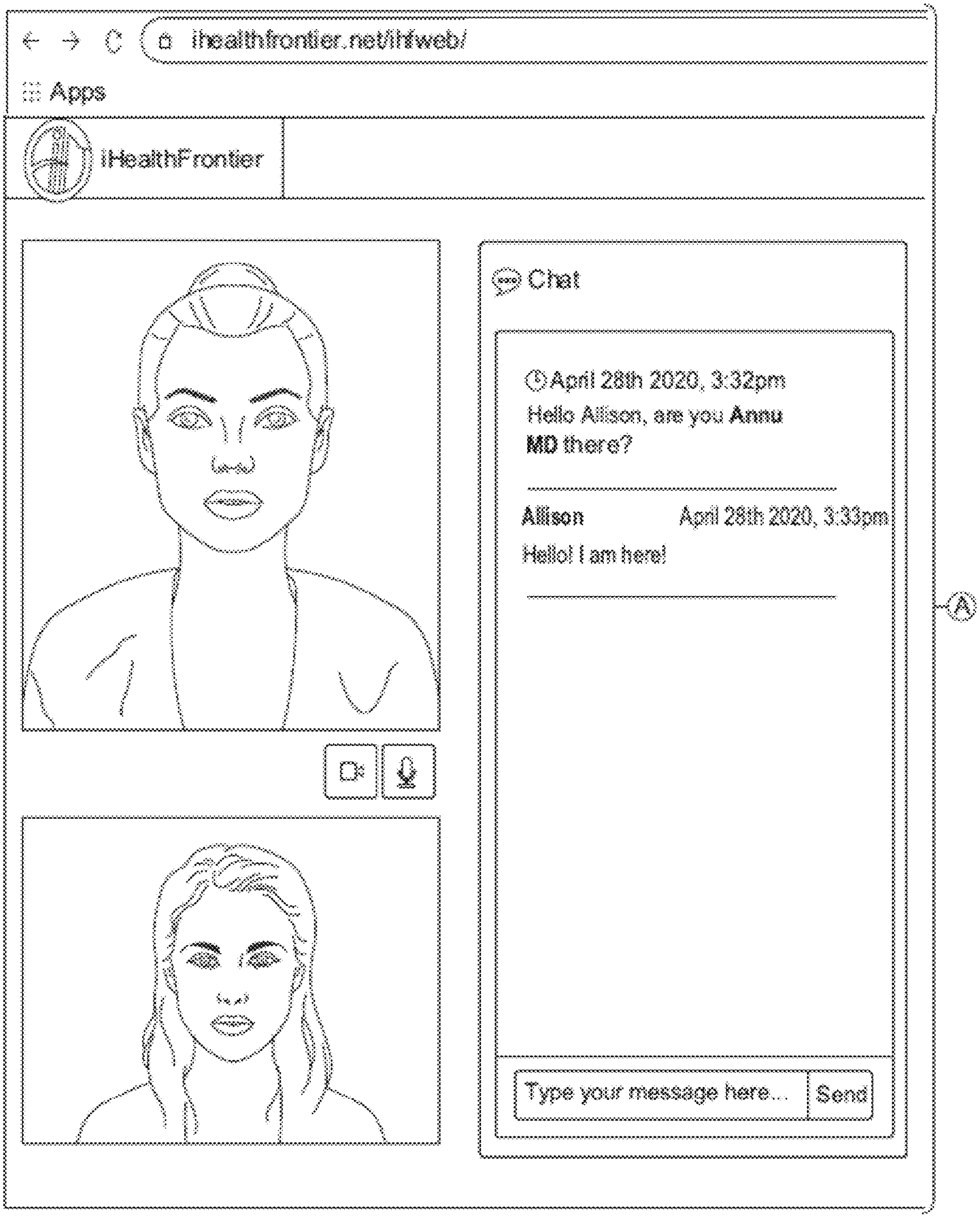
FIG. 2 illustrates a communication interface, in accordance with embodiments of the application.
Figure 2:
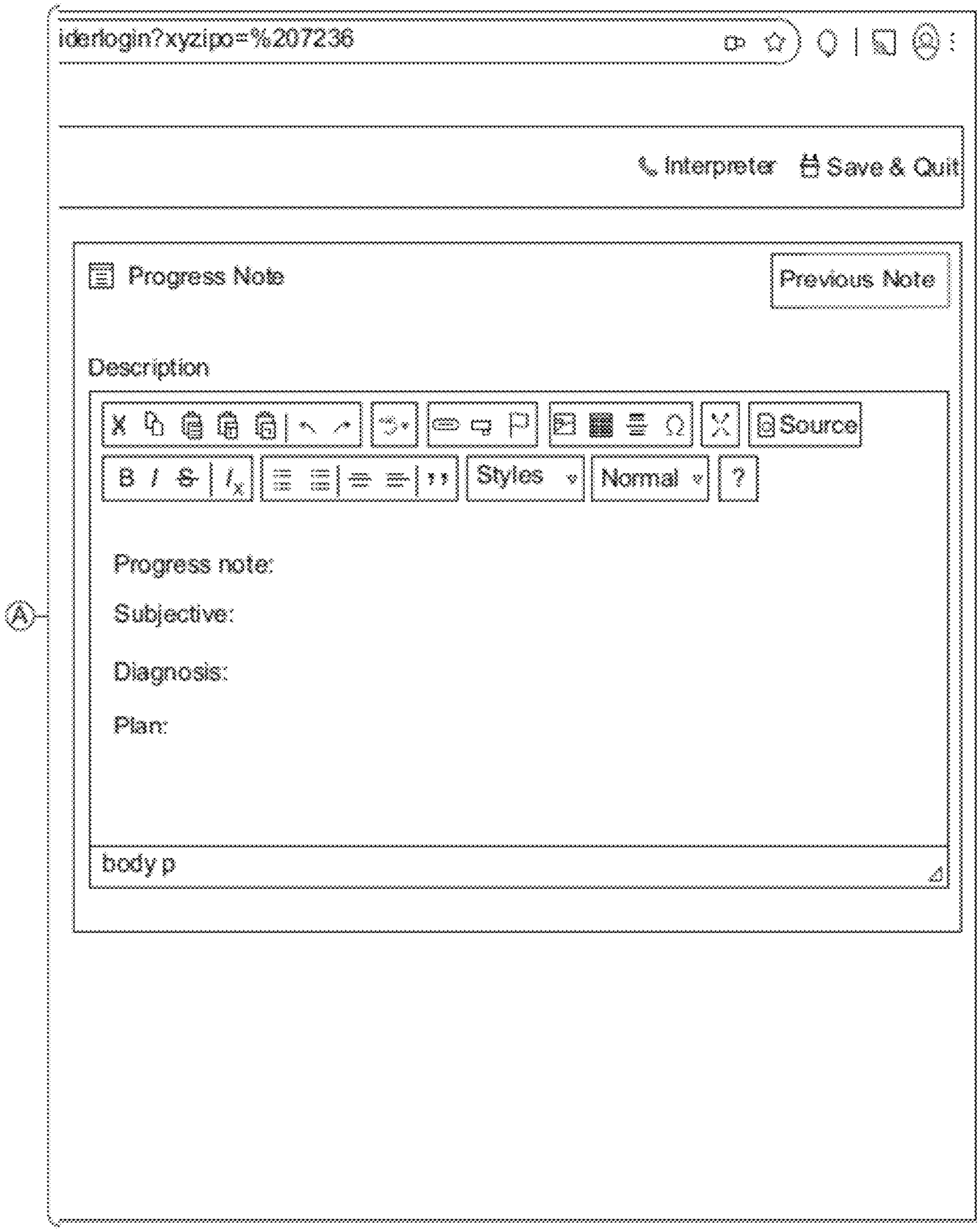

FIG. 2 illustrates an communication interface, in accordance with embodiments of the application. Data may be received at medical software platform 102 when captured through the communication interface. For example, a patient and a physician may visually see each other and speak via microphones and speakers incorporated with their individual user devices. In other examples, the patient and physician may exchange text messages or other forms of communication. As the communication is occurring, the physician entity may generate additional user data for the patient, which can be stored with the user file in medical software platform 102, including progress notes, subjective outcome, diagnosis, or health care plan based on what was discussed. The information may be stored directly to patient data store 112 for real-time data gathering and updates.

Returning to FIG. 1, one or more user devices 130 may be implemented. Each user device 130 may comprise a hardware processor (e.g., one or more central processing units (CPUs), semiconductor-based microprocessors, and/or other hardware devices) suitable for retrieval and execution of instructions stored in a machine-readable storage medium. The hardware processor may fetch, decode, and execute instructions to control processes or operations for optimizing the system during run-time. As an alternative or in addition to retrieving and executing instructions, hardware processor may include one or more electronic circuits that include electronic components for performing the functionality of one or more instructions, such as a field programmable gate array (FPGA), application specific integrated circuit (ASIC), or other electronic circuits.

The machine-readable storage medium may be any electronic, magnetic, optical, or other physical storage device that contains or stores executable instructions. This may include a Random Access Memory (RAM), non-volatile RAM (NVRAM), an Electrically Erasable Programmable Read-Only Memory (EEPROM), a storage device, an optical disc, and the like.

In some examples, user devices 130 may each correspond with one or more stakeholders can have authentication credentials (e.g., login username and password, etc.). User devices 130 may transmit the authentication credentials to an user interface associated with medical software platform 102. Once authenticated, the user may view and/or modify the patient data accessed from patient data store 112. This information may only be accessed by logging into the system.

To help increase data security of medical software platform 102, access and transmissions of the data may be restricted. In some examples, neither the patient data nor past or future therapies may be transmitted from medical software platform 102 to any user device 130. The transmissions may be limited to processed data or generated reports. In other examples, only authenticated users with medical or legal clearance may access confidential data (e.g., medical treatments, health information, patient responses to medical or legal questions, etc.), which may further increase security of the data collected.

Physician user device 130A may be operated by a physician or agent of the physician that is providing medical care to the patient. These users are the providers involved in the care of a patient, including for example, primary care physicians, ancillary care providers including psychologists, chiropractors, acupuncturists, and specialists like orthopedic surgeons.

Nurse case manager user device 130B may be operated by a nurse case manager. The nurse case manager may be responsible for helping a patient with one or more pain symptoms to obtain the medical care that he or she needs.

Healthcare provider user device 130C may be operated by a healthcare provider. Although the healthcare provide may be a physician, the healthcare provider may comprise any doctor of medicine who is authorized to practice medicine or surgery, including podiatrists, dentists, clinical psychologists, optometrists, chiropractors, nurse practitioners, nurse-midwives, clinical social workers, physician assistants, or other entities who are authorized to practice under state law and who are performing within the scope of their practice as defined under state law.

Physician user device 130A, nurse case manager user device 130B, or healthcare provider user device 130C may be responsible for providing additional information in association with an incomplete healthcare record from the medical provider. For example, medical software platform 102 may identify that patient data that is incomplete (e.g., missing treatments, health data, profile data, etc.) and generate and transmit an alert through notification module 108 to request the missing records from one of these entities.

Claims adjuster user device 130D may be operated by a claims adjuster. A claims adjuster investigates a source of a pain (e.g., if it was at work and/or associated with a worker compensation claim) to determine whether the claimant can receive care pursuant to one or more predefined rules. Claims adjusters can handle many cases, answer many telephone calls and emails, and sift through volumes of paperwork.

Employer user device 130E may be operated by an employer of the patient. The employer may provide a place of employment for the patient (e.g., where the patient works and was injured). Employer user device 130E may access aggregated patient data (e.g., associated with an occupation, recovery time, etc.) to help improve workplace conditions and help prevent future injuries.

Patient user device 130F may be operated by a patient and/or employee of the employer. Patient may seek care for his/her injury from a physician. Patient user device 130F may access medical software platform 102 through a web browser or other software application stored on patient user device 130F to help identify a status of a medical treatment, therapy, or claim.

Patient user device 130F may also include an interface to view reports or alerts generated by medical software platform 102 either locally or remotely from the device. Patient user device 130F may access medical software platform 102 via a web-based interface. The patient profile may be incorporated with the recommendations locally at the user device or remotely at medical software platform 102 as well.

In some examples, patient user device 130F may provide one or more therapies from therapies module 107 of medical software platform 102, including therapies using AI, robotics, and AR/VR/MR/XR. The therapies may be displayed at the user interface of patient user device 130F, which can receive selections from the user and provide feedback to medical software platform 102 in response to generate patient or therapy data (stored in patient data store 112).

In some examples, physician user device 130A, healthcare provider user device 130C, and patient user device 130F can access patient specific communication. Patient specific communication may be transmitted via a notification and the patient can access this by authenticating and browsing to medical software platform 102 (e.g., via a portal).

Various user devices may be operated by attorneys involved in a dispute related to a source of the pain (e.g., whether it was work related and corresponds with a workers compensation claim), including patient's attorney user device 130G and employer's attorney user device 130H. Patient's attorney user device 130G may be operated by a patient's attorney and employer's attorney user device 130H may be operated by an employer's attorney.

Fee negotiator user device 130I may be operated by a fee negotiator. The fee negotiator may act as a middle man between two entities (e.g., hospitals and an insurance provider) to help align costs with industry standards and eliminate exorbitant claims through negotiation.

Insurance provider user device 130J may be operated by an insurance provider. The insurance provider may provide workers compensation insurance (or other business insurance) to an employer of the patient. The workers compensation insurance provides benefits to employees who suffer work-related injuries, illnesses, or other pain.

Figure 3:
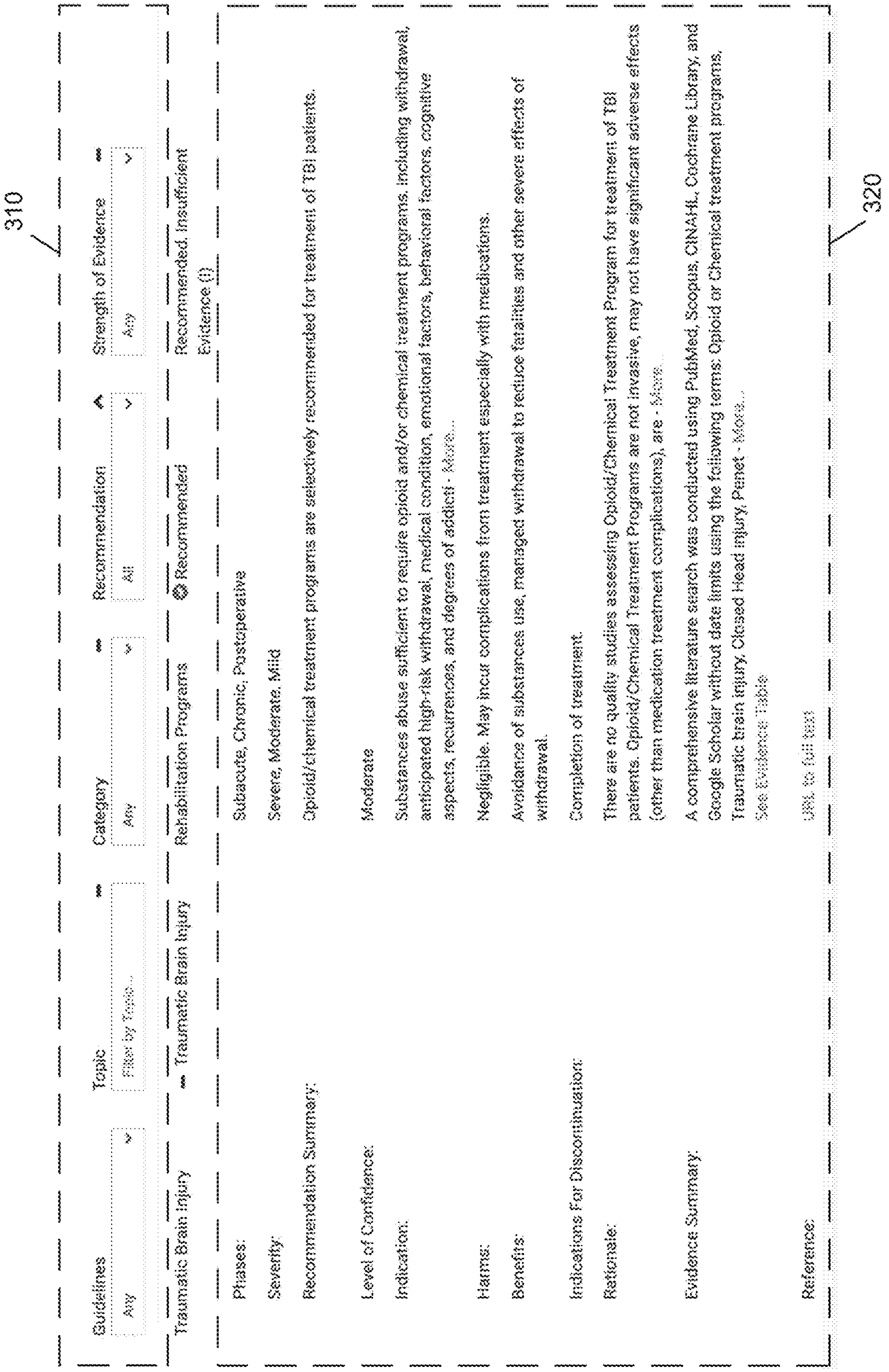
FIG. 3 illustrates sample data gathering and symptoms, in accordance with embodiments of the application.

FIG. 3 illustrates sample data gathering and symptoms in accordance with embodiments of the application. In this example, a filtering tool 310 may be provided at the user device 130 to identify one or more guidelines, topics, categories, recommendations, or strength of evidence. When the user selects one or more of these filtering identifiers, medical treatment or therapy options can be displayed on the interface to assist with treatment options.

For example, the user may provide a "traumatic brain injury" as one of the filtering options. The interface may identify whether rehabilitation programs are recommended and whether there is sufficient evidence for recommending the rehabilitation program in response to a traumatic brain injury diagnosis.

The interface may also provide additional information 320 associated with the patient's symptoms. For example, for the "traumatic brain injury" illustration, the additional information may include phases of the injury, severity of the injury, recommendation summary, level of confidence, indications of pain or injury, harms, benefits, indications for discontinuation of the treatment, rationale for providing or not providing the treatment, and evidence summary. In some examples, a link to further information may also be provided.

Figure 4:
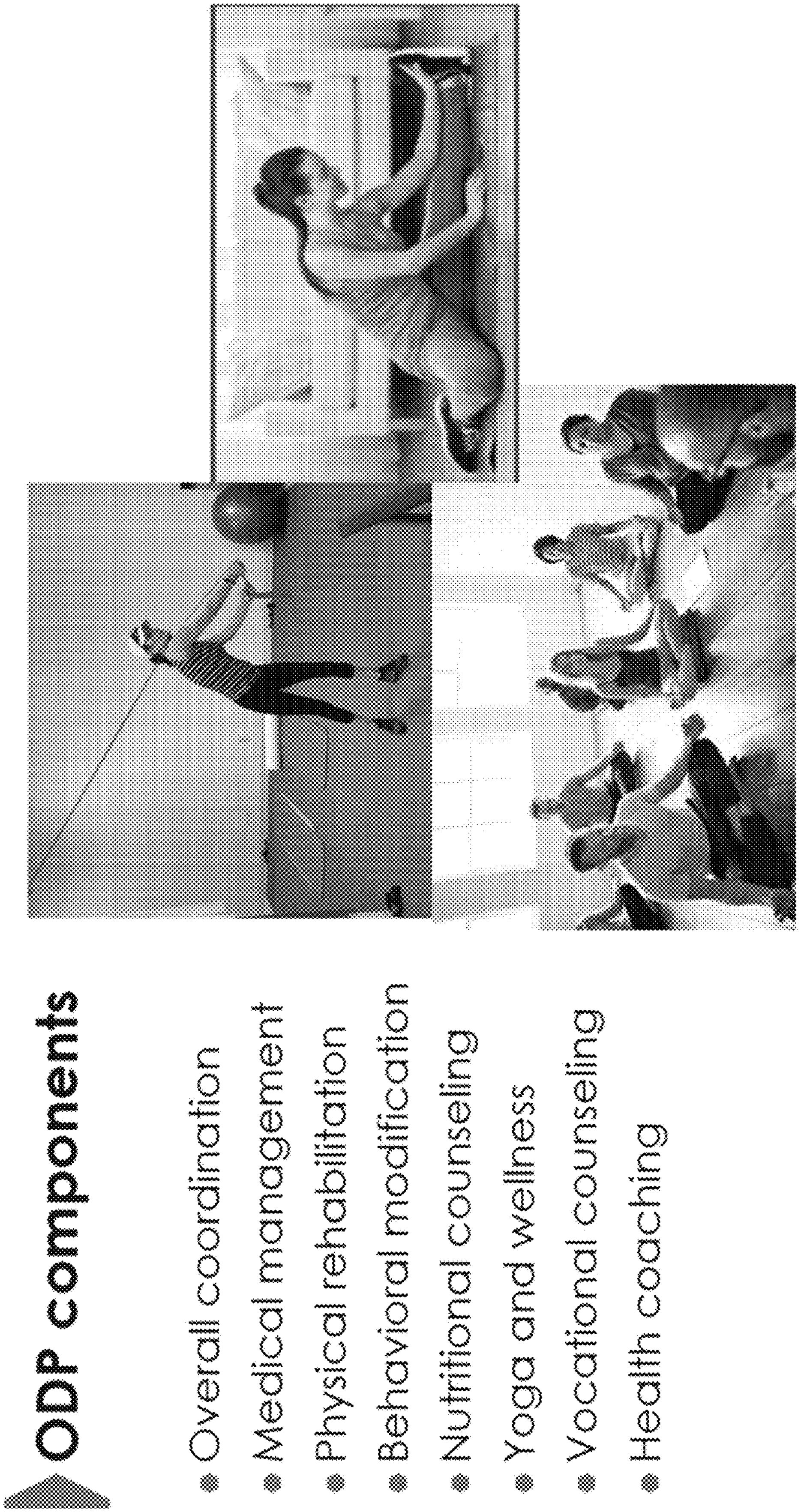
FIG. 4 illustrates sample therapies, in accordance with embodiments of the application.

FIG. 4 illustrates sample therapies in accordance with embodiments of the application. Illustrative therapies may include improving overall coordination, medical treatment management, physical rehabilitation, behavioral modification, nutritional counseling, yoga and wellness, vocational counseling, and/or health coaching. Depending on the medical diagnosis, a corresponding treatment plan may be determined from available treatments stored in therapy data store 116.

Figure 5:
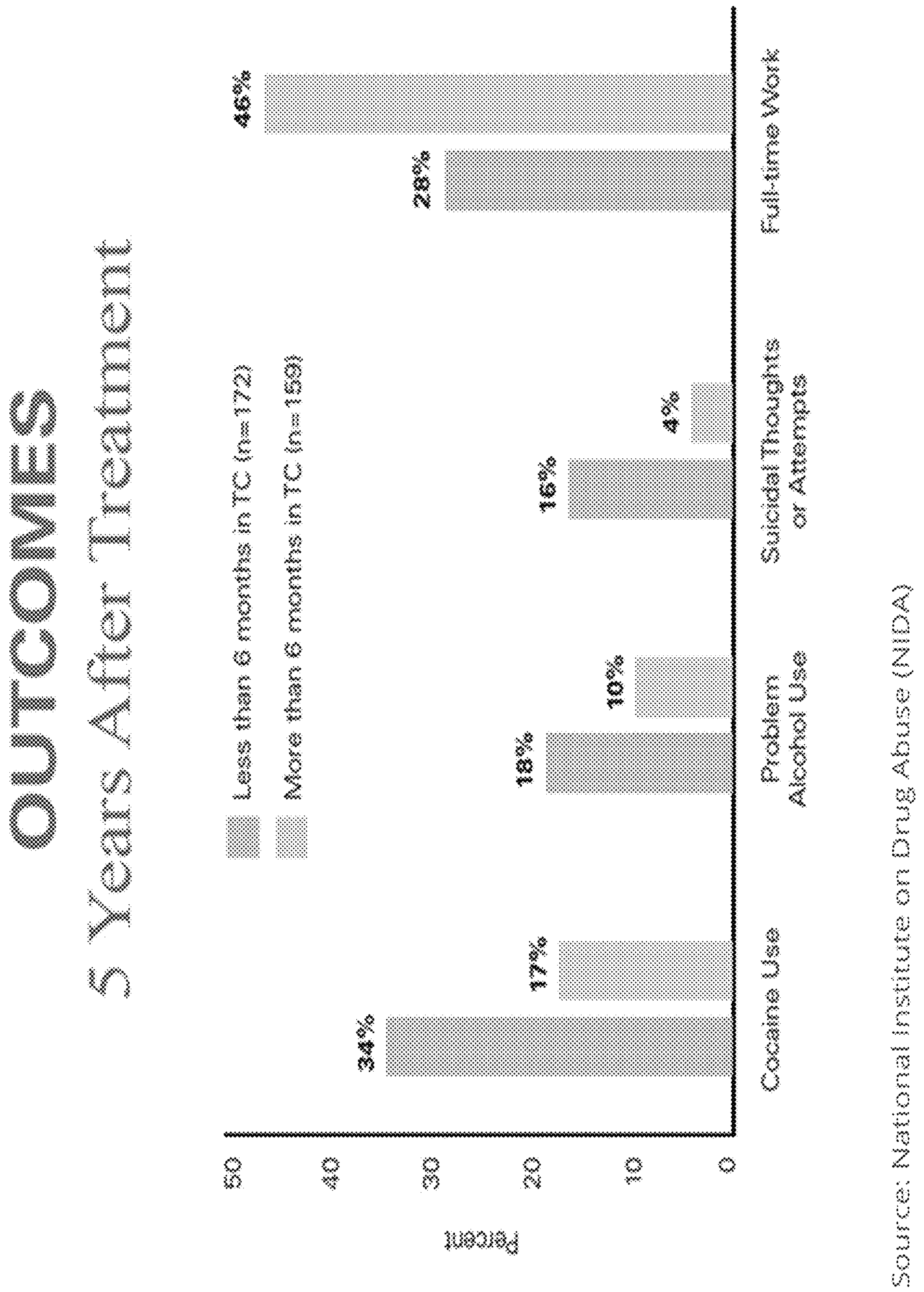
FIG. 5 illustrates outcomes from implementing one or more therapies via the medical software platform, in accordance with embodiments of the application.

FIG. 5 illustrates outcomes from implementing one or more therapies via the medical software platform, in accordance with embodiments of the application. In this illustration, patient results from following the therapy recommendations are provided, where the patient has implemented the therapies recommended with the assistance of the medical software platform 102.

Figure 6:
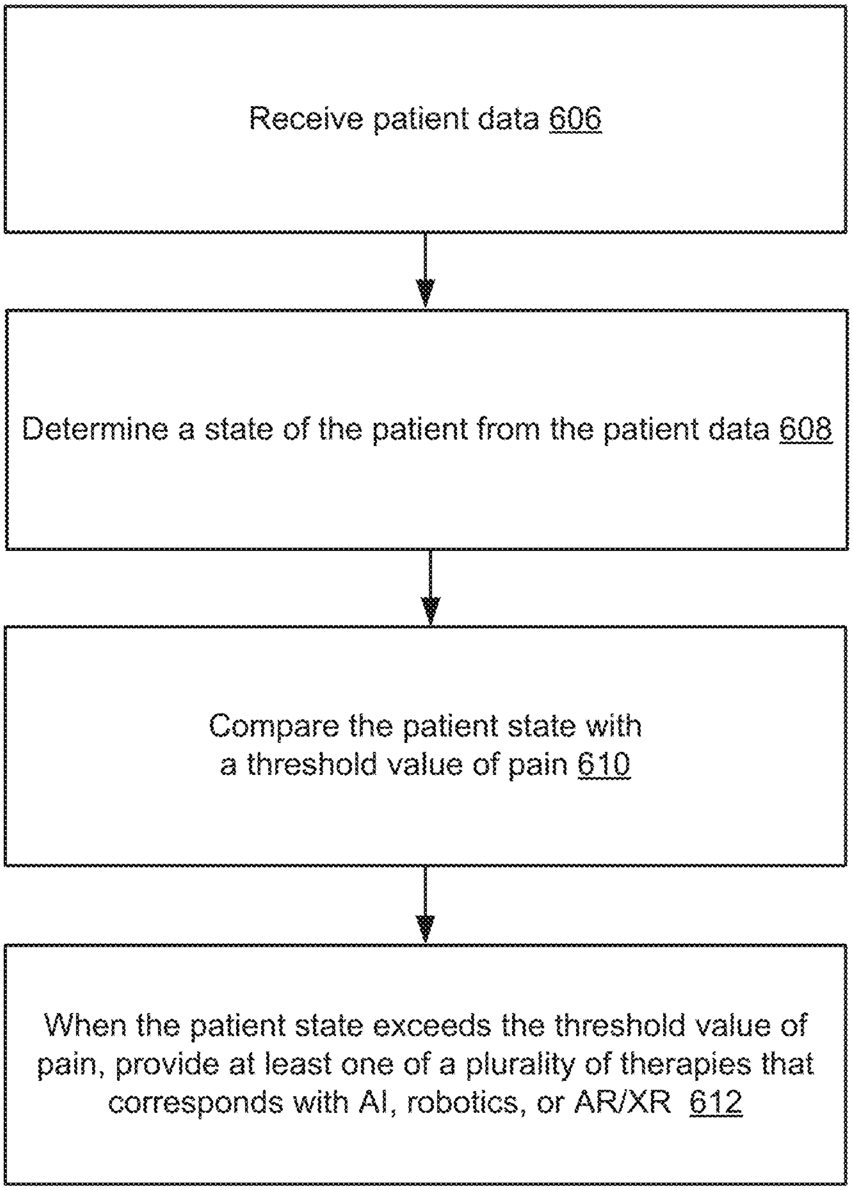
FIG. 6 illustrates a method for providing medical therapies, in accordance with embodiments of the application.

FIG. 6 illustrates a method for determining medical therapies, in accordance with embodiments of the application. The method may be implemented by patient user device 130F of FIG. 1.

At 606, patient data may be received. For example, medical software platform 102 may receive patient data associated with a patient. The patient may be experiencing a pain symptom.

At 608, a state of a patient may be determined. For example, medical software platform 102 may determine a state of the patient from the patient data.

At 610, the state of the patient may be compared with a threshold value of pain. For example, medical software platform 102 may compare the state of the patient with the threshold value of pain. The threshold value may vary by patient type or patient data, including a patient's health history, demographic data, environmental data, or socioeconomic data.

At 612, at least one of the plurality of therapies may be provided to the patient when the patient state exceeds the threshold value of pain, where the plurality of therapies include artificial intelligence (AI), robotics, or augmented or mixed reality (AR)(XR). The state of the patient, patient profile, or other analytics may help determine which therapy to select and provide to the patient. In other examples, the therapies may include yoga, physical therapy, psychology, nutrition, pain management, medications, live or pre-recorded lectures, counseling, meditation, and the like, or more technological therapies using artificial intelligence (AI), robotics, or extended reality (XR) technology.

Figure 7:
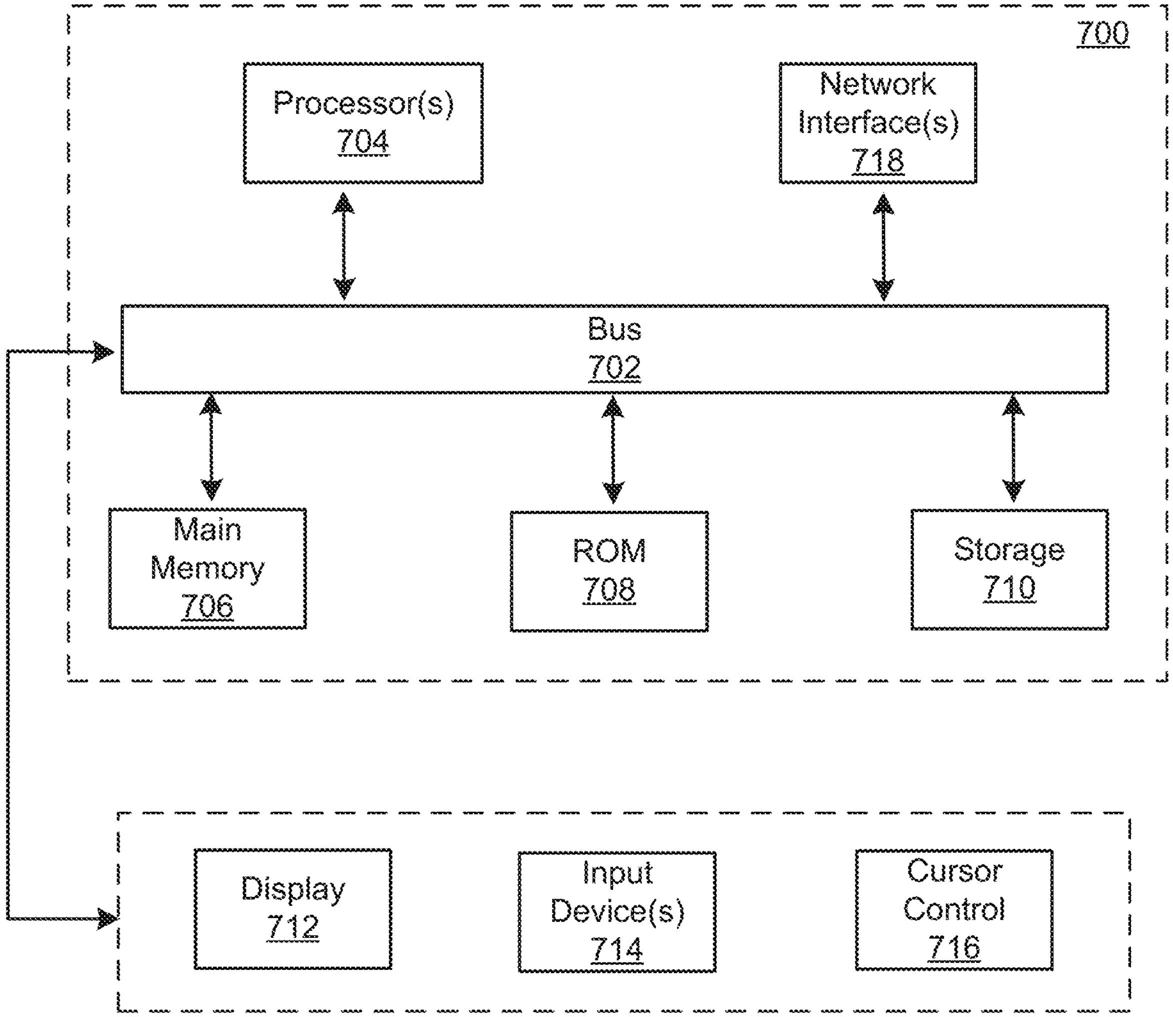
FIG. 7 is an example computing component that may be used to implement various features of embodiments described in the present disclosure.

FIG. 7 depicts a block diagram of an example computer system 700 in which various of the embodiments described herein may be implemented. The computer system 700 includes a bus 702 or other communication mechanism for communicating information, one or more hardware processors 704 coupled with bus 702 for processing information. Hardware processor(s) 704 may be, for example, one or more general purpose microprocessors.

The computer system 700 also includes a main memory 706, such as a random access memory (RAM), cache and/or other dynamic storage devices, coupled to bus 702 for storing information and instructions to be executed by processor 704. Main memory 706 also may be used for storing temporary variables or other intermediate information during execution of instructions to be executed by processor 704. Such instructions, when stored in storage media accessible to processor 704, render computer system 700 into a special-purpose machine that is customized to perform the operations specified in the instructions.

The computer system 700 further includes a read only memory (ROM) 708 or other static storage device coupled to bus 702 for storing static information and instructions for processor 704. A storage device 710, such as a magnetic disk, optical disk, or USB thumb drive (Flash drive), etc., is provided and coupled to bus 702 for storing information and instructions.

The computer system 700 may be coupled via bus 702 to a display 712, such as a liquid crystal display (LCD) (or touch screen), for displaying information to a computer user. An input device 714, including alphanumeric and other keys, is coupled to bus 702 for communicating information and command selections to processor 704. Another type of user input device is cursor control 716, such as a mouse, a trackball, or cursor direction keys for communicating direction information and command selections to processor 704 and for controlling cursor movement on display 712. In some embodiments, the same direction information and command selections as cursor control may be implemented via receiving touches on a touch screen without a cursor.

The computing system 700 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "component," "engine," "system," "database," data store," and the like, as used herein, can refer to logic embodied in hardware or firmware, or to a collection of software instructions, possibly having entry and exit points, written in a programming language, such as, for example, Java, C or C++. A software component may be compiled and linked into an executable program, installed in a dynamic link library, or may be written in an interpreted programming language such as, for example, BASIC, Perl, or Python. It will be appreciated that software components may be callable from other components or from themselves, and/or may be invoked in response to detected events or interrupts. Software components configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware components may be comprised of connected logic units, such as gates and flip-flops, and/or may be comprised of programmable units, such as programmable gate arrays or processors.

The computer system 700 may implement the techniques described herein using customized hard-wired logic, one or more ASICs or FPGAs, firmware and/or program logic which in combination with the computer system causes or programs computer system 700 to be a special-purpose machine. According to one embodiment, the techniques herein are performed by computer system 700 in response to processor(s) 704 executing one or more sequences of one or more instructions contained in main memory 706. Such instructions may be read into main memory 706 from another storage medium, such as storage device 710. Execution of the sequences of instructions contained in main memory 706 causes processor(s) 704 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 710. Volatile media includes dynamic memory, such as main memory 706. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 702. Transmission media can also take the form of acoustic or light waves, such as those generated during radio-wave and infra-red data communications.

The computer system 700 also includes a communication interface 718 coupled to bus 702. Communication interface 718 provides a two-way data communication coupling to one or more network links that are connected to one or more local networks. For example, communication interface 718 may be an integrated services digital network (ISDN) card, cable modem, satellite modem, or a modem to provide a data communication connection to a corresponding type of telephone line. As another example, communication interface 718 may be a local area network (LAN) card to provide a data communication connection to a compatible LAN (or WAN component to communicated with a WAN). Wireless links may also be implemented. In any such implementation, communication interface 718 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the world wide packet data communication network now commonly referred to as the "Internet." Local network and Internet both use electrical, electromagnetic or optical signals that carry digital data streams. The signals through the various networks and the signals on network link and through communication interface 718, which carry the digital data to and from computer system 700, are example forms of transmission media.

The computer system 700 can send messages and receive data, including program code, through the network(s), network link and communication interface 718. In the Internet example, a server might transmit a requested code for an application program through the Internet, the ISP, the local network and the communication interface 718.

The received code may be executed by processor 704 as it is received, and/or stored in storage device 710, or other non-volatile storage for later execution.

Each of the processes, methods, and algorithms described in the preceding sections may be embodied in, and fully or partially automated by, code components executed by one or more computer systems or computer processors comprising computer hardware. The one or more computer systems or computer processors may also operate to support performance of the relevant operations in a "cloud computing" environment or as a "software as a service" (SaaS). The processes and algorithms may be implemented partially or wholly in application-specific circuitry. The various features and processes described above may be used independently of one another, or may be combined in various ways. Different combinations and sub-combinations are intended to fall within the scope of this disclosure, and certain method or process blocks may be omitted in some implementations. The methods and processes described herein are also not limited to any particular sequence, and the blocks or states relating thereto can be performed in other sequences that are appropriate, or may be performed in parallel, or in some other manner. Blocks or states may be added to or removed from the disclosed example embodiments. The performance of certain of the operations or processes may be distributed among computer systems or computers processors, not only residing within a single machine, but deployed across a number of machines.

As used herein, a circuit might be implemented utilizing any form of hardware, software, or a combination thereof. For example, one or more processors, controllers, ASICs, PLAs, PALs, CPLDs, FPGAs, logical components, software routines or other mechanisms might be implemented to make up a circuit. In implementation, the various circuits described herein might be implemented as discrete circuits or the functions and features described can be shared in part or in total among one or more circuits. Even though various features or elements of functionality may be individually described or claimed as separate circuits, these features and functionality can be shared among one or more common circuits, and such description shall not require or imply that separate circuits are required to implement such features or functionality. Where a circuit is implemented in whole or in part using software, such software can be implemented to operate with a computing or processing system capable of carrying out the functionality described with respect thereto, such as computer system 700.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

What is claimed is:

1. A method for providing pain management in a technological environment using a robotic device, an extended reality (XR) device, and a medical software platform, the method comprising:

tracking, using the medical software platform, a pain symptom of a patient using electronic timestamps to determine a rate of change in pain level associated with the pain symptom of the patient over time;

matching the determined rate of change in pain level with a therapy regime to select the therapy regime from a plurality of therapy regimes stored in a therapy data store of the medical software platform, wherein the plurality of therapy regimes are indexed at least in part based on the determined rate of change in pain level;

providing a first therapy of the therapy regime by controlling the robotic device to apply pressure to an anatomical region of the patient associated with pain symptom; and providing a second therapy of the therapy regime by causing the XR device to display a virtual environment designed to distracting the patient while providing the first therapy, wherein the robotic device comprises sensors that measure an amount of pressure applied to the patient while providing the first therapy.

2. The method of claim 1, further comprising:

tracking effectiveness of the first therapy or the second therapy using patient feedback received from a patient user device.

3. The method of claim 2, further comprising:

comparing the patient feedback with other patient data to determine correlations between feedback and the electronic timestamps or the determined rate of change in pain level; and providing a third therapy based on the effectiveness of the first therapy or the second therapy.

4. The method of claim 1, wherein the first therapy or the second therapy is based on an occupation of the patient.

5. The method of claim 1, further comprising:

altering a future therapy based on a comparison between the patient and other patients.

6. The method of claim 1, further comprising:

comparing patient recovery with approvals or denials of other therapies;

predicting a timeline for recovery associated with the approvals or the denials of the other therapies; and providing the timeline for recovery to a patient user device or a physician user device.

7. The method of claim 1, wherein the therapy regime stored in the therapy data store of the medical software platform comprises at least one of rehabilitation therapies, nutritional counseling, yoga, mindfulness, or vocational counseling.

8. A system comprising:

a robotic device;

an extended reality (XR) device;

memory; and one or more processors configured to execute machine readable instructions stored in the memory for performing a method comprising:

tracking a pain symptom of a patient using electronic timestamps to determine a pattern of pain level associated with the pain symptom of the patient over time;

correlating the determined pattern of pain level to a plurality of pre-defined pain profiles stored in the memory;

based on the correlating, selecting a first pre-defined pain profile from the plurality of pre-defined pain profiles;

matching the first pre-defined pain profile with a first pre-defined therapy regime to select the first pre-defined therapy regime from a plurality of pre-defined therapy regimes stored in a therapy data store of the memory, wherein the plurality of pre-defined therapy regimes are indexed at least in part based on pain profile;

providing a first therapy of the first pre-defined therapy regime by controlling the robotic device to apply pressure to an anatomical region of the patient associated with pain symptom; and providing a second therapy of the first pre-defined therapy regime by causing the XR device to display a virtual environment designed to distract the patient while providing the first therapy, wherein the robotic device comprises sensors that measure an amount of pressure applied to the patient while providing the first therapy.

9. The system of claim 8, wherein the method further comprises:

tracking effectiveness of the first therapy or the second therapy using patient feedback received from a patient user device.

10. The system of claim 9, wherein the method further comprises:

comparing the patient feedback with other patient data to determine correlations between feedback and the electronic timestamps or the determined pattern of pain; and providing a third therapy based on the effectiveness of the first therapy or the second therapy.

11. The system of claim 8, wherein the first therapy or the second therapy is based on an occupation of the patient.

12. The system of claim 8, wherein the method further comprises:

altering a future therapy based on a comparison between the patient and other patients.

13. The system of claim 8, wherein the method further comprises:

comparing patient recovery with approvals or denials of other therapies;

predicting a timeline for recovery associated with the approvals or the denials of the other therapies; and providing the timeline for recovery to a patient user device or a physician user device.

14. The system of claim 8, wherein the first pre-defined therapy regime stored in the therapy data store comprises at least one of rehabilitation therapies, nutritional counseling, yoga, mindfulness, or vocational counseling.

15. The system of claim 8, wherein determining the pattern of pain level associated with the pain symptom of the patient over time comprises determining a rate of change in pain level.

16. A non-transitory machine readable media storing a plurality of instructions executable by one or more processors, the plurality of instructions when executed by the one or more processors cause the one or more processors to:

track a pain symptom of a patient using electronic timestamps to determine a pattern of pain level associated with the pain symptom of the patient over time;

correlate the determined pattern of pain level to a plurality of pre-defined pain profiles stored in a pain profile data store;

based on the correlating, select a first pre-defined pain profile from the plurality of pre-defined pain profiles;

match the first pre-defined pain profile with a first pre-defined therapy regime to select the first pre-defined therapy regime from a plurality of pre-defined therapy regimes stored in a therapy data store, wherein the plurality of pre-defined therapy regimes are indexed at least in part based on pain profile;

provide a first therapy of the first pre-defined therapy regime by controlling a robotic device to apply pressure to an anatomical region of the patient associated with pain symptom; and provide a second therapy of the first pre-defined therapy regime by causing an extended reality (XR) device to distract the patient while providing the first therapy, wherein the robotic device comprises sensors that measure an amount of pressure applied to the patient while providing the first therapy.

17. The non-transitory machine readable media of claim 16, the plurality of instructions when executed by the one or more processors further cause the one or more processors to:

track effectiveness of the first therapy or the second therapy using patient feedback received from a patient user device.

18. The non-transitory machine readable media of claim 17, the plurality of instructions when executed by the one or more processors further cause the one or more processors to:

compare the patient feedback with other patient data to determine correlations between feedback and the electronic timestamps or the determined pattern of pain; and provide a third therapy based on the effectiveness of the first therapy or the second therapy.

19. The non-transitory machine readable media of claim 16, wherein determining the pattern of pain level associated with the pain symptom of the patient over time comprises determining a rate of change in pain level.

* * * * *